United States Patent
Onishi et al.

(10) Patent No.: US 6,717,013 B2
(45) Date of Patent: Apr. 6, 2004

(54) PERFLUOROALKYLATED ANILINE COMPOUND AND PROCESS FOR PRODUCING THE SAME

(75) Inventors: Masanobu Onishi, Tondabayashi (JP); Akihiko Yoshiura, Tondabayashi (JP); Eiji Kohno, Habikino (JP); Kenji Tsubata, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 10/437,381

(22) Filed: May 14, 2003

(65) Prior Publication Data

US 2003/0204104 A1 Oct. 30, 2003

Related U.S. Application Data

(63) Continuation of application No. 10/206,769, filed on Jul. 29, 2002, now Pat. No. 6,600,074, which is a continuation of application No. 09/450,228, filed on Nov. 29, 1999, now abandoned.

(30) Foreign Application Priority Data

| Nov. 30, 1998 | (JP) | ............................. | 10-340354 |
| Dec. 4, 1998 | (JP) | ............................. | 10-361844 |
| Aug. 13, 1999 | (JP) | ............................. | 11-229304 |

(51) Int. Cl.⁷ .............................................. C07C 211/00
(52) U.S. Cl. ....................................... 564/305; 564/442
(58) Field of Search .............................. 564/305, 442

(56) References Cited

U.S. PATENT DOCUMENTS

| 5,900,509 | A | | 5/1999 | Mais et al. | |
| 6,114,584 | A | | 9/2000 | Mandal | |
| 6,235,939 | B1 | | 5/2001 | Marhold | |
| 6,316,484 | B1 | * | 11/2001 | Flygare et al. | ............... 514/403 |
| 6,316,658 | B1 | | 11/2001 | Yoshida et al. | |
| 6,399,272 | B1 | * | 6/2002 | Lee et al. | ................. 430/270.1 |
| 6,410,737 | B1 | * | 6/2002 | Ancel et al. | ................. 546/311 |
| 6,461,587 | B1 | * | 10/2002 | Platzek et al. | ........... 424/9.323 |
| 6,482,860 | B1 | * | 11/2002 | Flygare et al. | ............... 514/602 |
| 6,509,503 | B1 | | 1/2003 | Angel et al. | |

FOREIGN PATENT DOCUMENTS

| EP | 0206915 A | 12/1986 |
| EP | 484223 | 5/1992 |
| EP | 0919542 A2 | 6/1999 |
| EP | 09369212 A1 | 8/1999 |
| GB | 1535234 | 12/1978 |
| JP | 02255644 | 10/1990 |
| JP | 02258746 | 10/1990 |
| JP | 05051536 | 3/1993 |
| WO | WO9316959 | 9/1993 |

OTHER PUBLICATIONS

Chemical Abstract XP002132431, Aug. 1009.
Chemical Abstract XP002132432, Nov. 1987.
Chemical Abstract XP002132433, Oct. 1993.
Chemical Abstract 128:127799, 1997.
Chemical Abstract 127:65290, 1997.
Chemical Abstract 125:195389, 1996.
Chemical Abstract 124:320151, 1996.
Chemical Abstract 120:297958, 1993.
Chemical Abstract 117:251010, 1992.
Chemical Abstract 117:235802, 1992.
Chemical Abstract 114:23460, 1990.
Chemical Abstract 105:190550, 1985.
Betzemeier et al. Angew. Chem Int. Bd. Engl. vol. 36, No. 13, pp. 2623–2624 (1997).
Chen et al. J. Chem. Soc. Perkins Trans. vol. 1, No. 20, pp. 2457–2462 (1993).
Gerys et al. J. Org. Chem. (USSR) vol. 21, No. 9, Part 1, pp. 1694–1699 (1985).
Huang et al. Chinese J. Chem. vol. 10, No. 2, pp. 180–185 (1992).
Matsui et al. J. Fluorine Chem. vol. 57, pp. 209–217 (1992).
Strbwkowski et al. I Heterocycl. Commun. vol. 3, No. 2, pp. 109–113 (1997).
Strbwkowski et al. II. Tetrahedron Letters. vol. 37, No. 27, pp. 4655–4658 (1996).
Tordeux et al. J. Chem. Soc. Perkins Trans, vol. 1, No. 8, pp. 2293–2299 (1990).
Wakselman et al. J, Chem. Soc. Chem. Comm. vol. of 1987, pp. 1701–1703.
Yoshino et al. Nihon Yukagakkaishi vol. 45, No. 2, pp. 171–179 (1996).

* cited by examiner

*Primary Examiner*—Deborah C. Lambkin
(74) *Attorney, Agent, or Firm*—Paul E. White, Jr.; Manelli Denison & Selter

(57) ABSTRACT

The present invention provides an aniline derivative represented by the formula (I)

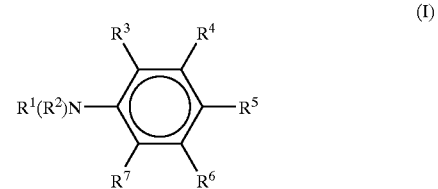

(I)

wherein $R^1$ and $R^2$ are each H, $(C_{1-12})$alkyl, $(C_{3-8})$cycloalkyl, hydroxy$(C_{1-12})$alkyl, hydroxycarbonyl $(C_{1-12})$alkyl, $(C_{1-6})$-alkoxycarbonyl$(C_{1-6})$alkyl, —$COR^8$, wherein $R^8$ is H, halo-$(C_{1-12})$alkyl, $(C_{3-8})$cycloalkyl or (substituted) phenyl, $COOR^9$, wherein $R^9$ is a halo$(C_{1-6})$alkyl group, (substituted) phenyl or (substituted) benzyl; $R^3$, $R^4$, $R^5$, $R^6$ and $R^7$ are each H, halogen, OH, nitro, halo$(C_{1-12})$alkylthio, (substituted) amino-$(C_{1-2})$alkyl, (substituted) phenyl, (substituted) benzyl, amino, —$N(R^{10})R^{11}$ wherein $R^{10}$ and $R^{11}$ are each H, alkyl, cycloalkyl, (substituted) phenyl, (substituted) benzyl, —$COR^8$ or $COOR^9$, or $(C_{2-27})$perfluoroalkyl, etc., and a process for producing the aniline derivative. According to the process of the present invention, perfluoroalkylaniline derivatives can be obtained by using various anilines as the substrate with a high position selectivity and high yield.

2 Claims, No Drawings

PERFLUOROALKYLATED ANILINE COMPOUND AND PROCESS FOR PRODUCING THE SAME

This application is a continuation of Ser. No. 10/206,769 filed Jul. 29, 2002, now U.S. Pat. No. 6,600,074, and is a continuation of Ser. No. 09/450,228 filed Nov. 29, 1999 now abandoned.

BACKGROUND OF THE INVENTION

1. Field of the Invention

The present invention relates to a novel perfluoroalkylated aniline derivative, which is a useful intermediate, to an industrially advantageous novel process for producing the aniline derivative and to a novel aniline derivative, which is also a useful intermediate, derived from the said derivative.

Perfluoroalkylated aniline derivatives are useful as intermediates or raw materials for the synthesis of agricultural chemicals, pharmaceuticals, surface active agents, rubber materials, mold release agents, water and oil repellents, optical materials, gas separation membrane materials, resist materials, antifouling paints, weatherproofing paints, paper-converting agents, textile-treating agents, heat resistant resins, etc. (cf, for example, "Saisentan Gijutsu (Advanced Technologies) in Halogen Chemicals", published by CMC); for use in agricultural chemicals, in particular, they are useful compounds as raw materials for the agricultural and horticultural insecticides disclosed in EP 919542. With regard to perfluoroalkylanilines, however, virtually no simple and useful process for the production thereof has hitherto been reported.

The present invention provides a novel process for producing perfluoroalkylated, paticularly secondary perfluoroalkylated aniline derivatives and novel, useful intermediates which can be produced by the process.

2. Related Art Statement

Known processes for producing perfluoroalkylated aniline derivatives include, for example, [A] a method which comprises introducing a perfluoroalkyl group by replacing the halogen atom of a halogenated nitrobenzene and then reducing the nitro group into the amino group and a method which comprises introducing a perfluoroalkyl group by replacing the halogen atom of a halogenated aniline. The following processes have been reported with regard to producing perfluoroalkylated aniline derivatives according to either of the above-mentioned methods.

(a) Processes wherein the reaction is conducted by using a perfluoroalkyl halide as the perfluoroalkylating agent in the presence of metallic copper are described, for example, in (1) Tetrahedron, 1969, 25, 5921, (2) Offenlegungsschrift 26 06 982, (3) J. Chem. Soc. Japan, 1972, 1876, (4) J. Chem. Soc. Perkin Trans. 1, 1980, 661, and (5) Bull. Chem. Soc. Jpn., 1992, 65, 2141. These processes, however, are industrially disadvantageous in that previous introduction of a halogen to an appropriate position of a nitrobenzene or an aniline is necessary, excess of copper is required, and further the reaction temperature is unfavorably high.

(b) Processes wherein the reaction is conducted by using a perfluoroalkylcarboxylic acid metal salt as the perfluoroalkylating agent in the presence of copper iodide are described, for example, in (1) J. Chem. Soc. Perkin Trans, 1, 1988, 921 and (2) Synth. Commun., 1988, 18, 965. These processes are also industrially disadvantageous in that they require a nitrobenzene having a halogen atom introduced to its appropriate position, it needs a large amount of copper iodide, and the reaction temperature is unfavorably high.

(c) A process wherein the reaction is conducted by using a perfluoroalkyltrialkylsilane as the perfluoroalkylating agent in the presence of potassium fluoride and copper iodide is described, for example, in (1) Tetrahedron Lett., 1991, 32, 91. This process also is industrially unsuitable in that it requires a nitrobenzene having a halogen atom introduced to its appropriate position, the perfluoroalkylating agent is expensive and the use of stoichiometric amounts of potassium fluoride and copper iodide is necessary.

(d) Processes wherein a perfluoroalkene is made to react on a fluoronitrobenzene in the presence of fluorine anions are described, for example, in (1) J. Chem. Soc. (c), 1968, 2221, (2) J. Org. Synth Chem. Japan, 1969, 27, 993, (3) J. Chem. Soc. Japan, 1976, 198 and (4) Tetrahedron, 1995, 51, 13167. These processes are not suitable for general use because the substrates which can be used are restricted to those compounds which have been strongly activated by an electron attractive groups, e.g., perfluoronitrobenzenes and dinitrofluorobenzenes and hence the compounds which can be prepared by these processes are greatly restricted in their structure.

[B] The following have been reported as to the method of directly perfluoroalkylating an aniline.

(a) Processes wherein a perfluoroalkyl halide is made to react on an aniline in the presence of a reducing agent are described, for example, in (1) EP 298,803 (JP-A-1-100135), (2) EP 206,951 (JP-A-62-26241), (3) J. Chem. Soc. Perkin Trans., 1, 1990, 2293, (4) J. Chem. Soc., Chem. Commun., 1987, 1701 and (5) J. Heterocyclic Chem., 1994, 31, 1413. In these processes, the yield of the intended product is low to medium and the selectivity is very poor as to the position to be perfluoroalkylated, hence they cannot be expected to be useful in practice.

(b) A process wherein the perfluoroalkylated compound is irradiated with light in the presence of a reducing agent is disclosed, for example in JP-A-57-18638. This process also gives a low to medium yield of the product and a very poor selectivity, and hence presents a low practical usefulness.

(c) Processes wherein a perfluoroalkyl halide or a perfluoroalkylsulfonyl chloride is heated in the presence of a metal catalyst are described, for example, in (1) J. Fluorine Chem., 1983, 22, 541, (2) JP-A-57-142923, (3) WO 93/16969 (Jap. Nat. Publ. (Kohyo) 7-504414, U.S. Pat. No. 5,276,194), (4) JP-A-3-240739 and (5) EP-0, 114,359. Among these, the processes of (1) and (2) give a low to medium yield, show a low selectivity, require a large amount of copper, need a high temperature and long reaction time, and thus are industrially disadvantageous. The process of (3) has the disadvantages of requiring an expensive catalyst and high reaction temperature and showing substantially no selectivity. The processes of (4) and (5) cannot be expected to be useful in practice because they require an expensive catalyst, high temperature and long time and moreover no embodiment treating an aniline is described.

(d) Processes wherein the peroxide of a perfluoroalkylcarboxylic acid is used are described, for example, in (1) JP-A-3-109362, (2) JP-A-5-246933, and (3) Bull.

Chem. Soc. Jpn., 1995, 68, 1042. These processes, however, are disadvantageous in that they require the use of a hazardous peroxide and the substrate to be used is restricted to phenylenediamines or quinones and hence they are not suited to general use.

(e) A process wherein a perfluoroalkylhalide is treated under a high temperature and an applied pressure is described in U.S. Pat. No. 3,281,426, but the process is industrially disadvantageous in that it require a high temperature and a special apparatus.

(f) Processes wherein a perfluoroalkylcarboxylic acid is treated with xenon difluoride are described, for example, in (1) J. Org. Chem., 1988, 53, 4582, and (2) JP-A-6-184065. These processes have the disadvantages in that they require a large amount of highly toxic reagent and both the yield and the selectivity are not sufficiently high.

SUMMARY OF THE INVENTION

An object of the present invention is, overcomming the above-mentioned various problems of the prior techniques, to provide a process for producing a perfluoroalkyl-substituted aniline which uses raw materials, reagents and catalysts which are inexpensive, easily available, safe and easy to handle, is based on reactions which are mild, simple and give a high yield and selectivity, does not produce a large amount of wastes and is economically highly efficient also in the aftertreatment. Another object of the present invention is to provide a novel perfluoroalkylated aniline derivative, particularly a secondary perfluoroalkylated aniline derivative, which can be used for versatile and valuable applications.

DETAILED DESCRIPTION OF THE INVENTION

The present inventions have made are extensive study to solve the above-mentioned problems and resultantly found a novel process for production and a novel intermediate compound which can be obtained by the process.

According to the present invention, there are provided an aniline derivative represented by the formula (I)

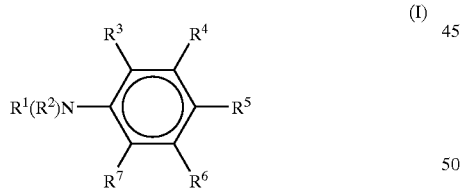

wherein $R^1$ and $R^2$ may be the same or different and each denote a hydrogen atom, $(C_{1-12})$alkyl group, $(C_{3-8})$ cycloalkyl group, hydroxy$(C_{1-12})$ alkyl group, hydroxycarbonyl$(C_{1-2})$ alkyl group, $(C_{1-6})$alkoxycarbonyl $(C_{1-6})$ alkyl group, —$COR^8$ (wherein $R^8$ is a hydrogen atom, $(C_{1-12})$alkyl group, halo$(C_{1-12})$alkyl group, $(C_{3-8})$cycloalkyl group, phenyl group or phenyl group substituted with 1–5 groups, which may be the same or different, selected from the group consisting of cyano group, nitro group, hydroxyl group, halogen atom, $(C_{1-6})$ alkyl group, halo$(C_{1-6})$alkyl group, $(C_{1-6})$alkoxy group, halo$(C_{1-6})$alkoxy group, carboxyl group and $(C_{1-6})$alkoxycarbonyl group) or $COOR^9$ (wherein $R^9$ is a $(C_{1-6})$alkyl group, halo$(C_{1-6})$alkyl group, phenyl group, phenyl group substituted with 1–5 groups, which may be the same or different, selected from the group consisting of cyano group, nitro group, hydroxyl group, halogen atom, $(C_{1-6})$alkyl group, halo$(C_{1-6})$alkyl group, $(C_{1-6})$ alkoxy group, halo$(C_{1-6})$ alkoxy group, carboxyl group and $(C_{1-6})$alkoxycarbonyl group, benzyl group or benzyl group substituted on the ring with 1–5 groups, which may be the same or different, selected from the group consisting of cyano group, nitro group, hydroxyl group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxy-carbonyl group);

$R^3$, $R^4$, $R^5$, $R^6$ and $R^7$ may be the same or different and each denote a hydrogen atom, halogen atom, hydroxyl group, nitro group, $(C_{1-12})$alkyl group, halo$(C_{1-12})$alkyl group, $(C_{1-12})$alkoxy group, halo$(C_{1-12})$alkoxy group, $(C_{1-12})$alkylthio group, halo$(C_{1-12})$alkylthio group, $(C_{1-6})$alkylthio $(C_{1-6})$alkyl group, hydroxy $(C_{1-6})$alkyl group, amino $(C_{1-6})$alkyl group, amino$(C_{1-6})$alkyl group substituted with one or two $(C_{1-6})$alkyl groups which may be the same or different, phenyl group, phenyl group substituted with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group and halo$(C_{1-6})$alkoxy group, phenoxy group, phenoxy group substituted with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group and halo$(C_{1-6})$alkoxy group, benzyl group, benzyl group substituted on the ring with 1–5 groups, which may be the same or different, selected from the group consisting of cyano group, nitro group, halogen atom, $(C_{1-6})$alkyl group, halo$(C_{1-6})$alkyl group, $(C_{1-6})$ alkoxy group and halo$(C_{1-6})$alkoxy group, —$N(R^{10})R^{11}$ (wherein $R^{10}$ and $R^{11}$ may be the same or different and are each a hydrogen atom, $(C_{1-12})$alkyl group, $(C_{3-8})$cycloalkyl group, phenyl group, phenyl group substituted with 1–5 groups, which may be the same or different, selected from the group consisting of cyano group, nitro group, hydroxyl group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxycarbonyl group, benzyl group, benzyl group substituted on the ring with 1–5 groups, which may be the same or different, selected from the group consisting of cyano group, nitro group, hydroxyl group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxycarbonyl group, —$COR^8$ wherein $R^8$ has the same meaning as defined above, or $COOR^9$ wherein $R^9$ has the same meaning as defined above, further, $R^{10}$ and $R^{11}$ may conjointly from a $(C_{3-6})$alkylene group) or $(C_{2-27})$perfluoroalkyl group;

and further, $R^1$ or $R^2$ and $R^3$ or $R^7$ may conjointly form a $(C_{2-4})$alkylene group, and $R^3$, $R^4$, $R^5$, $R^6$ and $R^7$ may form, with their two adjacent substituents joined together, a $(C_{3-5})$alkylene group or $(C_{1-2})$ alkylenedioxy group, and at least one of $R^3$, $R^4$, $R^5$, $R^6$ and $R^7$ must be a $(C_{2-27})$-perfluoroalkyl group; provided that (1) when $R^1$, $R^2$, $R^4$ and $R^7$ are each a hydrogen atom, $R^3$ is a fluorine atom and $R^6$ is a hydrogen atom, fluorine atom or chlorine atom, or when $R^1$, $R^2$, $R^3$ and $R^6$ are each a hydrogen atom, $R^7$ is a fluorine atom and $R^4$ is a hydrogen atom, fluorine atom or chlorine atom, then $R^5$ must not be a pentafluoroethyl group or heptafluoro-n-propyl group, (2) when $R^1$ and $R^2$ are each a hydrogen atom, $R^3$ is a methyl group and $R^4$, $R^6$ and $R^7$ are simultaneously each a hydrogen atom, or when $R^1$ and $R^2$ are each a hydrogen atom, $R^7$ is a methyl group and $R^3$, $R^4$ and $R^6$ are simultaneously each a hydrogen atom, then $R^5$ must not be a pentafluoroethyl group, heptafluoropropyl group, nonafluoro-n-butyl group or nonafluoro-sec-butyl group, (3) when $R^1$ and $R^2$ are each a hydrogen atom, $R^3$ is a methyl group and $R^5$, $R^6$ and $R^7$ are simultaneously each a hydrogen atom, or when $R^1$ and $R^2$ are each a hydrogen atom, $R^3$, $R^5$ and $R^6$ are simultaneously each a hydrogen atom and $R^7$ is a methyl group, then $R^4$ must not be a pentafluoroethyl group, (4) when $R^1$ and $R^2$ are each a hydrogen atom, $R^3$ is a methyl group and $R^4$, $R^5$ and $R^7$ are simultaneously each a hydrogen atom, then $R^6$ must not be a pentafluoroethyl group; or when $R^1$ and $R^2$ are each a hydrogen atom, $R^3$, $R^5$ and $R^6$ are simultaneously each a hydrogen atom and $R^7$ is a methyl group, then $R^4$ must not be a pentafluoroethyl group, (5) when $R^1$, $R^2$, $R^4$, $R^6$ and $R^7$ are simultaneously each a hydrogen atom and $R^3$ is a chlorine atom or when $R^1$, $R^2$, $R^3$, $R^4$ and $R^6$ are simultaneously each a hydrogen atom and $R^7$ is chlorine atom, then $R^5$ must not be a pentafluoroethyl group, heptafluoropropyl group or nonafluoro-n-butyl group, (6) when $R^1$, $R^2$, $R^4$, $R^6$ and $R^7$ are simultaneously each a hydrogen atom and $R^3$ is an ethyl group, n-butyl group, methoxy group or trifluoromethyl group or when $R^1$, $R^2$, $R^3$, $R^4$ and $R^6$ are simultaneously each a hydrogen atom and $R^7$ is an ethyl group, n-butyl group, methoxy group or trifluoromethyl group, then $R^5$ must not be a pentafluoroethyl group, (7) when $R^1$ and $R^2$ are each a hydrogen atom and any four of the $R^3$, $R^4$, $R^5$, $R^6$ and $R^7$ are simultaneously each a hydrogen atom, then the remaining one of the $R^3$, $R^4$, $R^5$, $R^6$ and $R^7$ must not be a heptafluoroisopropyl group, (8) when $R^1$ and $R^2$ are each a methyl group and $R^3$, $R^4$, $R^6$ and $R^7$ are simultaneously each a hydrogen atom, then $R^5$ must not be a heptafluoroisopropyl group, (9) when $R^1$ and $R^2$ are each a methyl group and $R^3$, $R^5$, $R^6$ and $R^7$ are simultaneously each a hydrogen atom, then $R^4$ must not be a heptafluoroisopropyl group,

(10) when $R^1$ and $R^2$ are each a methyl group and $R^3$, $R^4$, $R^5$ and $R^7$ are simultaneously each a hydrogen atom, then $R^6$ must not be a heptafluoroisopropyl group,

(11) when $R^1$, $R^2$, $R^3$ and $R^6$ are simultaneously each a hydrogen atom, $R^4$ is an amino group and one of the $R^5$ and $R^7$ is a hydrogen atom, or when $R^1$, $R^2$, $R^4$ and $R^7$ are simultaneously each a hydrogen atom, $R^6$ is an amino group and one of the $R^3$ and $R^5$ is a hydrogen atom, then the other of the two must not be a heptafluoroisopropyl group,

(12) when $R^1$, $R^2$, $R^4$, $R^5$ and $R^7$ are simultaneously each a hydrogen atom and $R^6$ is a methoxy group or iodine atom, then $R^3$ must not be a heptafluoroisopropyl group, and

(13) when $R^1$, $R^2$, $R^3$, $R^5$ and $R^6$ are simultaneously each a hydrogen atom and $R^4$ is a methoxy group or iodine atom, then $R^7$ must not be a heptafluoroisopropyl group, and a process for producing an aniline derivative represented by the formula (I')

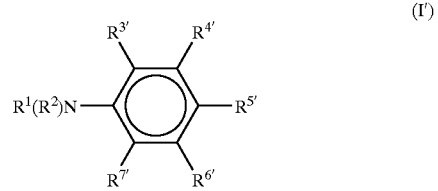

(I')

wherein $R^1$ and $R^2$ are the same as defined below for the formula (III), and $R^{3'}$, $R^{4'}$, $R^{5'}$, $R^{6'}$ and $R^{7'}$ may be the same or different and each denote a hydrogen atom, halogen atom, hydroxyl group, nitro group, $(C_{1-12})$alkyl group, halo$(C_{1-12})$alkyl group, $(C_{1-12})$alkoxy group, halo$(C_{1-12})$alkoxy group, $(C_{1-12})$alkylthio group, halo$(C_{1-12})$alkylthio group, $(C_{1-6})$alkylthio$(C_{1-6})$alkyl group, hydroxy$(C_{1-6})$alkyl group, amino$(C_{1-6})$alkyl group, amino$(C_{1-6})$alkyl group substituted with one or two $(C_{1-6})$alkyl groups which may be the same or different, phenyl group, phenyl group substituted with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group and halo$(C_{1-6})$alkoxy group, phenoxy group, phenoxy group substituted with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group and halo$(C_{1-6})$alkoxy group, benzyl group, benzyl group substituted on the ring with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group and halo$(C_{1-6})$alkoxy group, —N($R^{10}$)$R^{11}$ (wherein $R^{10}$ and $R^{11}$ are the same as defined below for the formula (III)) or $(C_{1-27})$perfluoroalkyl group, and at least one of the $R^{3'}$, $R^{4'}$, $R^{5'}$, $R^{6'}$ and $R^{7'}$ must be a $(C_{1-27})$perfluoroalkyl group, which comprises allowing an iodide represented by the formula (II)

I—$R^{12}$ (II)

wherein $R^{12}$ is a $(C_{1-27})$perfluoroalkyl group, to react with an aniline represented by the formula (III)

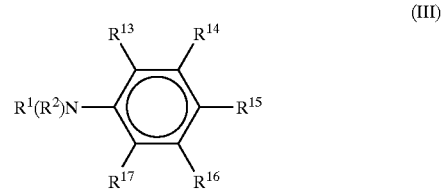

(III)

wherein $R^1$ and $R^2$ may be the same or different and each denote a hydrogen atom, $(C_{1-12})$alkyl group, $(C_{3-8})$cycloalkyl group, hydroxy$(C_{1-12})$alkyl group, hydroxycarbonyl$(C_{1-12})$alkyl group, $(C_{1-6})$alkoxycarbonyl$(C_{1-6})$alkyl group, —$COR^8$ (wherein $R^8$ is a hydrogen atom, $(C_{1-12})$alkyl group, halo$(C_{1-12})$alkyl group, $(C_{3-8})$cycloalkyl group, phenyl group or phenyl group substituted with 1–5 groups, which may be the same or different, selected from the group consisting of cyano group, nitro group, hydroxyl group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxycarbonyl group) or $COOR^9$ (wherein $R^9$ is a $(C_{1-6})$alkyl group, halo$(C_{1-6})$alkyl group, phenyl group, phenyl group substituted with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxycarbonyl group, benzyl group or benzyl group substituted on the ring with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxycarbonyl group);

$R^{13}$, $R^{14}$, $R^{15}$, $R^{16}$ and $R^{17}$ may be the same or different and such denote a hydrogen atom, halogen atom, hydroxyl group, nitro group, $(C_{1-12})$alkyl group, halo$(C_{1-12})$alkyl group, $(C_{1-12})$alkoxy group, halo$(C_{1-12})$alkoxy group, $(C_{1-12})$alkylthio group, halo-$(C_{1-12})$alkylthio group, $(C_{1-6})$alkylthio $(C_{1-6})$alkyl group, hydroxy$(C_{1-6})$alkyl group, amino$(C_{1-6})$alkyl group, amino-$(C_{1-6})$alkyl group substituted with one or two $(C_{1-6})$alkyl groups which may be the same or different, phenyl group, phenyl group substituted with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group and halo$(C_{1-6})$alkoxy group, phenoxy group, phenoxy group substituted with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group and halo$(C_{1-6})$alkoxy group, benzyl group, benzyl group substituted on the ring with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group and halo$(C_{1-6})$alkoxy group, or —N($R^{10}$)$R^{11}$ (wherein $R^{10}$ and $R^{11}$ may be the same or different and are each a hydrogen atom, $(C_{1-12})$alkyl group, $(C_{3-8})$cycloalkyl group, phenyl group, phenyl group substituted with 1–5 groups, which may be the same or different, selected from the group consisting of cyano group, nitro group, hydroxyl group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxycarbonyl group, benzyl group, benzyl group substituted on the ring with 1–5 groups, which may be the same or different, selected from the group consisting of cyano group, nitro group, hydroxyl group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxy-carbonyl group, —COR$^8$ (wherein R$^8$ is a hydrogen atom, $(C_{1-12})$alkyl group, halo$(C_{1-12})$alkyl group, $(C_{3-8})$cycloalkyl group, phenyl group or phenyl group substituted with 1–5 groups, which may be the same or different, selected from the group consisting of cyano group, nitro group, hydroxyl group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxycarbonyl group) or COOR$^9$(wherein R$^9$ is a $(C_{1-6})$alkyl group, halo$(C_{1-6})$alkyl group, phenyl group, phenyl group substituted with 1–5 groups, which may be the same or different, selected from the group consisting of cyano group, nitro group, halogen atom, $(C_{1-6})$alkyl group, halo$(C_{1-6})$alkyl group, $(C_{1-6})$alkoxy group, halo$(C_{1-6})$alkoxy group, carboxyl group and $(C_{1-6})$alkoxycarbonyl group, benzyl group, or benzyl group substituted on the ring with 1–5 groups, which may be the same or different, selected from the group consisting of cyano group, nitro group, halogen atom, $(C_{1-6})$alkyl group, halo$(C_{1-6})$alkyl, group, $(C_{1-6})$alkoxy group, halo$(C_{1-6})$alkoxy group, carboxyl group and $(C_{1-6})$alkoxycarbonyl group), further, $R^{10}$ and $R^{11}$ may conjointly form a $(C_{3-8})$alkylene group); and further, $R^1$ or $R^2$ and $R^{13}$ or $R^{17}$ may conjointly form a $(C_{2-4})$alkylene group and $R^{13}$, $R^{14}$, $R^{15}$, $R^{16}$ and $R^{17}$ may form, with their adjacent two substituents joined together, a $(C_{3-5})$ alkylene group or $(C_{1-2})$ alkylenedioxy group, in the presence of a reaction initiating agent.

The aniline derivatives referred to in the present invention includes those which are obtained directly by the above-mentioned reaction and those which are obtained by further modifying the aniline derivative thus formed, both of which are useful as intermediates for a variety of uses.

The process according to the present invention relates to a process for converting the hydrogen atom on the benzene ring of an aniline into a perfluoroalkyl group. The present invention relates to a process which exhibits a high selectivity to the perfluoroalkyl group introduction position for specific combinations of the substituents of the starting material aniline. However, the introduction position may vary according to the substituents of the anilines of the starting material and to the reaction conditions. Therefore, as a whole, the introduction site of the substituent is not restricted to a specific position alone.

In the description of the compounds in the present invention, in the definition of the respective substituents, "i" means iso-, "sec-" means secondary-, and "t-" means tertiary-; the "alkyl group" or "alkyl", which represents the alkyl moiety, may be either of a straight chain or of a branched chain unless otherwise defined; the "$(C_{1-12})$alkyl group" refers to an alkyl group having 1–12 carbon atoms and may be, for example, the methyl group, ethyl group, propyl group, isopropyl group, butyl group, isobutyl group, sec-butyl group, t-butyl group, neopentyl group, 1,2-dimethylpropyl group, hexyl group, heptyl group, octyl group, decyl group and dodecyl group.

The "halogen atom" refers to a chlorine atom, bromine atom, iodine atom or fluorine atom. The "halo-$(C_{1-12})$alkyl group" refers to a linear or branched alkyl group having 1–12 carbon atoms of which one or more hydrogen atoms have been substituted with one or more halogen atoms which may be the same or different and may be, for example, the difluoromethyl group, trifluoromethyl group, 2-chloroethyl group, 2-bromoethyl group, 2,2,2-trifluoroethyl group, 3-chlorobutyl group, 3-bromobutyl group, 1-chloropentyl group, 1-chlorohexyl group, 6-bromohexyl group and bromododecyl group.

The "$(C_{3-8})$cycloalkyl group" refers to a cyclic alkyl group having 3–8 carbon atoms and may be, for example, the cyclopropyl group, cyclobutyl group, cyclopentyl group, cyclohexyl group, cycloheptyl group and cyclooctyl group. The "$(C_{1-3})$alkyl$(C_{3-8})$cycloalkyl group" refers to a cycloalkyl group having 3–8 carbon atoms of which one or more of the hydrogen atoms have been substituted with one or more alkyl groups, which may be the same or different, selected from alkyl groups having 1–3 carbon atoms, e.g., the methyl group, ethyl group and isopropyl group.

The "$(C_{1-27})$perfluoroalkyl group" refers to an alkyl group having 1–27 carbon atoms of which the entire hydrogen atoms have been substituted with fluorine atoms, wherein the alkyl may be either of a straight chain or branched chain or cyclic, which may be interrupted by an oxygen atom, and may be, for example, the trifluoromethyl group, n-pentafluoroethyl groups, n-heptafluoropropyl group, heptafluoroisopropyl group, n-nonafluorobutyl group, sec-nonafluorobutyl group, nonafluoroisobutyl group, undecafluoroneopentyl group, undecafluoropentyl group, tridecafluorohexyl group, pentacosafluorododecyl group, -A$^1$-A$^2$-D (wherein A$^1$ represents (CF$_2$)$_l$ wherein l is an integer of 0 to 24, A$^2$ represents (CFY)$_m$, wherein Y is a fluorine atom or trifluoromethyl group and m is an integer of 0 or 1, and D represents the trifluoromethyl group), or

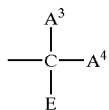

wherein A$^3$ and A$^4$ may be the same or different and each represent —(CF$_2$)$_n$—CF$_3$, wherein n is an integer of 0 to 15, or —(CF$_2$)$_p$O(CF$_2$)$_q$—CF$_3$, wherein p and q may be the same or different and each denote an integer of 0 to 12, further, A$^3$ and A$^4$ may conjointly form —(CF$_2$)$_r$—, wherein r is an integer of 2 to 7, and E is a fluorine atom. When the number of carbon atoms is 2 to 27, examples of the perfluoroalkyl group include the perfluoroalkyl groups shown above other than the trifluoromethyl group.

When a group contains an "alkoxy group" or "alkoxy" moiety, these terms mean a straight or branched chain alkoxy group. The "(C$_{1-6}$)alkoxy group" refers, for example, to the methoxy group, ethoxy group, isopropoxy group, sec-butoxy group, t-butoxy group, 1,2-dimethylpropoxy group and hexyloxy group. The "halo(C$_{1-6}$)alkoxy group" refers to a straight or branched chain alkoxy group of which one or more of the hydrogen atoms have been substituted with one or more halogen atoms which may be the same or different and may be, for example, the difluoromethoxy group, trifluoromethoxy group, 2-chloroethoxy group, 2-bromoethoxy group, 2,2,2-trifluoroethoxy group, 3-chlorobutoxy group, 3-bromobutoxy group, 1-chloropentyloxy group, 1-chlorohexyloxy group and 6-bromohexyloxy group.

The "(C$_{1-6}$)alkylthio group" refers, for example, to the methylthio group, ethylthio group, isopropylthio group, sec-butylthio group, t-butylthio group, 1,2-dimethyl-propylthio group and hexylthio group.

According to the process of the present invention, perfluoroalkylaniline derivatives can be obtained with a high position selectivity and high yield by using various anilines as the substrate. The process of the present invention makes it possible to use a catalytic amount of inexpensive reaction initiating agent and an easily recoverable reaction solvent which doubles as an extraction solvent, and further produces only a very small amount of wastes and hence is advantageous both environmentally and economically. Thus, the present invention provides novel perfluoroalkylaniline derivatives which have industrially versatile and valuable uses and a process for producing industrially valuable perfluoroalkylaniline derivatives, particularly secondary perfluoroalkylaniline derivatives.

A representative production process according to the present invention is described below, but the invention is not limited thereto.

Productive process 1

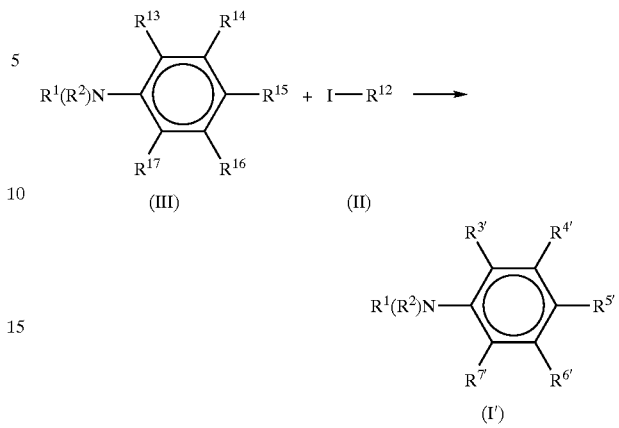

wherein R$^1$, R$^2$, R$^{3'}$, R$^{4'}$, R$^{5'}$, R$^{6'}$, R$^{7'}$, R$^{12}$, R$^{13}$, R$^{14}$, R$^{15}$, R$^{16}$ and R$^{17}$ are as defined above.

The aniline derivative represented by the formula (I')can be produced by reacting an aniline represented by the formula (III) with an iodide represented by the formula (II) in the presence of a reaction initiating agent, in the presence or absence of a base and in the presence or absence of an inert solvent. The present reaction may also be conducted by using as an inert solvent water and a water-insoluble inert solvent and using a phase transfer catalyst.

The reaction of the production process 1 is described in detail below, but the present invention is not to be limited to those specifically exemplified hereunder.

1. Reaction Materials
(1) Iodide

The iodide represented by the formula (II) used in the present invention may be, for example, perfluoroethyl iodide, perfluoroisopropyl iodide, perfluoro-n-propyl iodide, perfluoro-sec-butyl iodide, perfluorocyclopentyl iodide and tetrafluoro-1-trifluoromethoxy-1-iodoethane. R$^{12}$ is the formula (II) is preferably a secondary perfluoroalkyl group. Iodides whose perfluoroalkyl groups are of a long chain may also be used The reaction easily proceeds when the number of carbon atoms of the alkyl group is up to about 16.

(2) Anilines

Anilines represented by the formula (III) which may be used include, for example, aniline, fluoroaniline, chloroaniline, dichloroaniline, bromoaniline, 2-toluidine, 3-toluidine, 4-toluidine, 2-anisidine, 3,4-dimethoxyaniline, ethylaniline, isopropylaniline, 2-t-butylaniline, 2,6-dimethylaniline, N,N-dimethylaniline, 2,6-diethlaniline, N,N-diethylaniline, diisopropylaniline, 2-fluoro-3-methylaniline, 3-chloro-4-methylaniline, biphenylaniline, aminophenol, anisidine, ethoxyaniline, phenoxyaniline, dimethoxyaniline, phenylanisidine, phenylenediamine, methylthioaniline and N-methyltoluidine.

2. Reaction Initiating Agent

The reaction initiating agents which may be used include a reducing agent and light irradiation. The reducing agent may be, for example, dithionous acid salts, such as sodium dithionite and potassium dithionite, or zinc-aqueous sulfurous acid. The amount of the reducing agent is not particularly limited, but it is usually from about $\frac{1}{100}$ to about 2 equivalents, preferably in the range of $\frac{1}{10}$–1.2 equivalents, relative to 1 equivalent of the reaction material (anilines). The light source used for irradiation with light is not particularly limited so long as it can provide a sufficient energy to initiate the reaction and may be, for example, a high pressure mercury lamp.

The reducing agent and light irradiation as the reaction initiating agent may be used either singly or in combination of the two.

3. Phase Transfer Catalyst

The phase transfer catalysts which may be used include, for example, quaternary ammonium salts, such as tetrabutylammonium hydrogen sulfate and tetrabutylammonium bromide, organic phosphorus salt compounds, such as tetrabutylphosphonium bromide, and alkylpolyether alkylamine compounds, such as tris (methoxyethoxyethyl) amine. The use of a phase transfer catalyst is not always necessary but in some cases gives better results. The amount of the catalyst to be used is not particularly limited, but it is usually from about 1/500 to about 2 equivalents, preferably in the range from about 1/50 to about 1 equivalent relative to 1 equivalent of the reaction material (anilines).

4. Base

The bases which may be used are inorganic bases and organic bases. The inorganic bases may be, for example, alkali metal carbonates, such as sodium hydrogen carbonate, sodium carbonate and potassium carbonate, and alkali metal hydroxides, such as sodium hydroxide and potassium hydroxide. The organic bases may be, for example, triethylamine and 4-dimethylaminopyridine.

5. Inert Solvent

The inert solvent to be used is not particularly restricted so long as it does not markedly inhibit the progress of the reaction. It may be, for example, ether type solvents, such as diethylether, tetrahydrofuran, dioxane and t-butyl methyl ether, halogen-containing solvents, such as dichloroethane, inert benzene type solvents, such as nitrobenzene, ketone type solvents, such as acetone and cyclohexanone, ester type solvents, such as ethyl acetate, nitrile type solvents, such as acetonitrile and pivalonitrile, amide type solvents, such as dimethylformamide, and water. These inert solvents may be used each alone or as a mixture of two or more thereof.

Though depending also on the substituents of the raw material and the reaction conditions, the use of, for example, a nonpolar solvent as the inert solvent results, in many cases, in a good reaction selectivity and affords a more preferable reaction conditions. When a nonpolar solvent is used, the reaction system, as it is or, according to circumstances, with addition of a necessary amount of nonpolar solvent, can be subjected to an extraction operation; this is advantageous also in point of production cost.

When a phase transfer catalyst is used, the reaction may also be conducted in a two-phase system comprising a combination of water and a nonpolar solvent as the inert solvent. The inert solvent used can be selected as desired from the above-mentioned inert solvents, the use of a two phase system comprising water and an inert solvent yielding a good result.

6. Reaction Temperature

The reaction may be conducted at reaction temperatures approximately in the range from 0° C. to the boiling point of the solvent at the reaction conditions. The reaction is preferably conducted at about 0° C. to about 50° C. with advantage in industrial production.

7. Reaction Time

The reaction time varies depending on the reaction conditions, but it is usually from several minutes to several tens of hours, preferably from about 30 minutes to about 24 hours.

In the present reaction, after completion of the reaction, the intended product is isolated from the reaction system by a conventional method and then, according to necessity, subjected to purification, etc., whereby the intended product can be produced.

The aniline derivative represented by the formula (I) can also be produced by first producing an aniline derivative wherein $R^1$ and $R^2$ are each a hydrogen atom according to the process of the present invention and then producing the intended derivative by a conventional method. For example, acylation by a reaction with an acid halide in the presence of a base, N-alkylation by a reaction with an alkylating agent or formylation using formic acid can be applied. Further, substituents may be introduced additonally onto the benzene ring. For example, an alkylaminomethyl group can be introduced, according to the method described in Russ. Chem. Rev., 46, 891–903, by haloalkylation conducted in the presence of formaldehyde, hydrochloric acid, catalyst, such as zinc chloride, and solvent, followed by reaction with an amine.

EXAMPLES

The present invention is described in detail below with reference to Examples and Comparative Examples, but the invention is in no way limited thereto.

Example 1

Preparation of 4-heptafluoroisopropylaniline

To a liquid mixture of 20 ml of water and 20 ml of t-butyl methyl ether were added successively 1 g (10.8 mmoles) of aniline, 3.8 g (13 mmoles) of heptafluoroisopropyl iodides, 2.2 g (13 mmoles) of sodium dithionite, 1.1 g (13 mmoles) of sodium hydrogen carbonate and 0.4 g (1.2 mmoles) of tetrabutylammonium hydrogen sulfate, and the resulting mixture was stirred at room temperature for 8 hours. After separation of the organic layer, the aqueous layer was extracted with 20 ml of ethyl acetate, the extract was combined with the organic layer and washed successively with 2N aqueous hydrochloric acid solution, 5% aqueous sodium carbonate solution and saturated aqueous sodium chloride solution. The organic layer was dried with magnesium sulfate, filtered and the organic solvent was distilled off under reduced pressure to obtain the intended product. Yield: 83%

$^1$HNMR (CDCl$_3$/TMS) δ: 3.70(bs. 2H), 6.71(d. 2H), 7.35(d. 2H).

Example 2

Preparation of 2-fluoro-4-heptafluoro-isopropylaniline

A reaction was conducted in the same manner as in Example 1 for 8 hours except for using 2-fluoroaniline in place of aniline to obtain the intended product. Yield: 66%.

Gas chromatographic analysis made on the reaction product before the acid treatment revealed that the constituents were nearly the starting materials alone except for the above-mentioned intended product.

$^1$HNMR (CDCl$_3$/TMS) δ: 3.96(bs. 2H), 6.83(dd. 1H), 7.15–7.24(m. 2H).

Example 3

Preparation of 3-fluoro-4-heptafluoro-isopropylaniline

A reaction was conducted in the same manner as in Example 1 for 12 hours except for using 3-fluoroaniline in place of aniline to obtain the intended product. Yield: 36%

Gas chromatographic analysis made on the reaction product before the acid treatment revealed that the constituents were nearly the starting materials alone except for the above-mentioned intended product.

$^1$HNMR (CDCl$_3$/TMS) δ: 6.42(dd. 1H), 6.52(dd, 1H), 7.32(t. 1H).

Example 4
Preparation of 3-chloro-4-heptafluoro-isopropylaniline

A reaction was conducted in the same manner as in Example 1 for 12 hours except for using 3-chloroaniline in place of aniline to obtain the intended product. Yield: 4%

Gas chromatographic analysis made on the reaction product before the acid treatment revealed that the constituents were nearly the starting materials alone except for the above-mentioned intended product.

$^1$HNMR (CDCl$_3$/TMS) δ: 4.32(bs. 2H), 6.87(s, 1H), 6.93(dt. 1H), 7.33(d. 1H).

Example 5
Preparation of 2-methyl-4-heptafluoro-isopropylaniline

A reaction was conducted in the same manner as in Example 1 for 2 hours except for using 2-toluidine in place of aniline. The gas chromatographic analysis of the organic layer before the acid treatment revealed that the starting materials had disappeared almost completely, 2-methyl-4-heptafluoroisopropylaniline was 98% and 2-methyl-6-heptafluoroisopropylaniline was 0.7%, respectively in terms of area percentage, the ratio being 140:1. After-treatment was conducted in the same manner as in Example 1 to obtain the intended product. Yield: 96%

$^1$HNMR (CDCl$_3$/TMS) δ: 2.20(s. 3H), 3.86(bs. 2H), 6.715(d. 1H), 7.25(d. 1H), 7.255(s. 1H).

Example 6
Preparation of 2-methyl-4-heptafluoro-isopropylaniline

A reaction was conducted in the same manner as in Example 5 except for reducing the amount of sodium dithionite used to 1.3 mmoles. The gas chromatographic analysis of the organic layer before the acid treatment revealed that the starting materials had disappeared nearly completely, 2-methyl-4-heptafluoroisopropylaniline was 98% and 2-methyl-6-heptafluoroisopropylaniline was 0.9%, respectively in terms of area percentage, the ratio being about 110:1. After-treatment was conducted in the same manner as in Example 1 to obtain the intended product. Yield: 95%

Comparative Example 1
(Conducted Under the Reaction Conditions Described in Reference B-a-1)

To a liquid mixture of 5 ml of dimethylformamide and 1.5 ml of water were successively added 1.1 g (10.3 mmoles) of 2-toluidine, 3.6 g (12.2 mmoles) of heptafluoroisopropyl iodide, 1 g (5.7 mmoles) of sodium dithionite and 1 g (2.8 mmoles) of disodium hydrogen phosphate hydrate, and the resulting mixture was stirred overnight at room temperature. Water and ethyl acetate were added to the reaction mixture, the organic layer was separated, and the aqueous layer was extracted with 20 ml of ethyl acetate. The gas chromatographic analysis of the combined organic layer revealed that 2-methyl-4-heptafluoroisopropylaniline was 35%, 2-methyl-6-heptafluoroisopropylaniline was 4%, the ratio being 9.2:1, thus a substantial amount of a position isomer had formed, and further 58% of 2-toluidine of the starting material remained.

Example 7
Preparation of 3-methyl-4-heptafluoro-isopropylaniline

A reaction was conducted in the same manner as in Example 1 for 4 hours except for using 3-toluidine in place of aniline to obtain the intended product. Yield: 85%

$^1$HNMR (CDCl$_3$/TMS) δ: 2.41(d. 3H), 3.85(bs. 2H), 6.53(s. 1H), 6.54(d. 1H), 7.23(d. 1H).

Example 8
Preparation of 2-ethyl-4-heptafluoro-isopropylaniline

A reaction was conducted in the same manner as in Example 1 for 2 hours except for using 2-ethylaniline in place of aniline to obtain the intended product. Yield: 90%

$^1$HNMR (CDCl$_3$/TMS) δ: 1.27(t. 3H), 2.54(q. 2H1), 3.80(bs. 2H), 6.74(d. 1H), 7.24(d. 1H), 7.26(s. 1H).

Example 9
Preparation of 2-isopropyl-4-heptafluoro-isopropylaniline

A reaction was conducted in the same manner as in Example 1 for 2 hours except for using 2-isopropylaniline in place of aniline to obtain the intended product. Yield: 91%

$^1$HNMR (CDCl$_3$/TMS) δ: 1.28(d. 6H), 2.51(m. 1H), 4.50(bs. 2H), 6.77(d. 1H), 7.22(d. 1H), 7.33(s. 1H).

Example 10
Preparation of 2-amino-5-heptafluoro-isopropylphenol

A reaction was conducted in the same manner as in Example 1 for 2 hours except for using 2-aminophenol in place of aniline to obtain the intended product. Yield: 98%

$^1$HNMR (CDCl$_3$/TMS) δ: 6.76(d. 1H), 6.94(s. 1H), 6.985 (d. 1H).

In the same manner, 2-amino-5-heptafluoroisopropyl-4-methylphenol was obtained.

Physical property: solid

Example 11
Preparation of 4-heptafluoroisopropyl-1,2-phenylenediamine

A reaction was conducted in the same manner as in Example 1 for 2 hours except for using 1,2-phenylenediamine in place of aniline to obtain the intended product. Yield: 68%

$^1$HNMR (CDCl$_3$/TMS) δ: 6.91(d. 1H), 7.00(d. 1H), 7.17 (s. 1H).

Example 12
Preparation of 4-heptafluoroisopropyl-2-anisidine

A reaction was conducted in the same manner as in Example 1 for 2 hours except for using 2-anisidine in place of aniline to obtain the intended product. Yield: 80%

The gas chromatographic analysis of the reaction product before the acid treatment revealed that the constituents were nearly the starting materials alone except for the above-mentioned intended product.

$^1$HNMR (CDCl$_3$/TMS) δ: 3.875(s. 3H), 6.74(d. 1H), 7.00(s. 1H), 7.02(d. 1H).

Example 13
Preparation of 2-ethoxy-4-heptafluoro-isopropylaniline

A reaction was conducted in the same manner as in Example 1 for 2 hours except for using 2-ethoxyaniline in place of aniline to obtain the intended product. Yield: 91%

$^1$HNMR (CDCl$_3$/TMS) δ: 1.45(t. 3H), 4.09(q. 2H), 6.79 (d. 1H), 6.94(s. 1H), 7.01(d. 1H).

Example 14
Preparation of 4-heptafluoroisopropyl-2-methylthioaniline

A reaction was conducted in the same manner as in Example 1 for 2 hours except for using 2-methylthioaniline in place of aniline to obtain the intended product. Yield: 81%

The gas chromatographic analysis of the reaction product before the acid treatment revealed that the constituents were nearly the starting materials alone except for the above-mentioned intended product.

$^1$HNMR (CDCl$_3$/TMS) δ: 2.34(s. 3H), 3.80(bs. 2H), 6.78(d. 1H), 7.27(dd. 1H), 7.56(d. 1H).

Example 15
Preparation of 4-heptafluoroisopropyl-2,3-dimethylaniline

A reaction was conducted in the same manner as in Example 1 for 2 hours except for using 2,3-dimethylaniline in place of aniline to obtain the intended product. Yield: 72%

The gas chromatographic analysis of the reaction product before the acid treatment revealed that the constituents were nearly the starting materials alone except for the above-mentioned intended product.

$^1$HNMR (CDCl$_3$/TMS) δ: 2.11(s. 3H), 2.38(d. 3H), 6.594 (d. 1H), 7.15(d. 1H).

Example 16
Preparation of 4-heptafluoroisopropyl-2,5-dimethylaniline

A reaction was conducted in the same manner as in Example 1 for 2 hours except for using 2,5-dimethylaniline in place of aniline to obtain the intended product. Yield: 84%.

The gas chromatographic analysis of the reaction product before the acid treatment revealed that the constituents were nearly the starting materials alone except for the above-mentioned intended product.

$^1$HNMR (CDCl$_3$/TMS) b: 2.15(s. 3H), 2.38(d. 3H), 4.10 (bs. 2H), 6.54(s. 1H), 7.11(s. 1H).

Example 17
Preparation of 4-heptafluoroisopropyl-2,6-dimethylaniline

A reaction was conducted in the same manner as in Example 1 for 2 hours except for using 2,6-dimethylaniline in place of aniline to obtain the intended product. Yield: 95%, m.p.: 63.3–64.9° C.

$^1$HNMR (CDCl$_3$/TMS) δ: 2.21(s. 6H), 3.90(bs. 2H), 7.14(s. 2H).

Example 18
Preparation of 4-heptafluoroisopropyl-2,6-diethylaniline

A reaction was conducted in the same manner as in Example 1 for 2 hours except for using 2,6-diethylaniline in place of aniline to obtain the intended product. Yield: 96%.

$^1$HNMR (CDCl$_3$/TMS) δ: 1.28(t. 6H), 2.56(q. 4H), 3.90 (bs. 2H), 7.15(s. 2H).

Example 19
Preparation of 4-heptafluoroisopropyl-2,6-diisopropylaniline

A reaction was conducted in the same manner as in Example 1 for 2 hours except for using 2,6-diisopropylaniline in place of aniline to obtain the intended product. Yield: 86%

$^1$HNMR (CDCl$_3$/TMS) δ: 1.28(d. 12H), 2.86–2.99(m. 2H), 4.00(bs. 2H), 7.21(s. 2H).

Example 20
Preparation of 5-fluoro-4-heptofluoro-isopropyl-2-methylaniline

A reaction was conducted in the same manner as in Example 1 for 8 hours except for using 5-fluoro-2-methylaniline in place of aniline to obtain the intended product. Yield: 50%

The gas chromatographic analysis of the reaction product before the acid treatment revealed that the constituents were nearly the starting materials alone except for the above-mentioned intended product.

$^1$HNMR (CDCl$_3$/TMS) δ: 2.15(s. 3H), 3.80(bs. 2H), 6.43(d. 1H), 7.18(d. 1H).

Example 21
Preparation of 5-chloro-4-heptafluoro-isopropyl-2-methylaniline

A reaction was conducted in the same manner as in Example 1 for 12 hours except for using 5-chloro-2-methylaniline in place of aniline to obtain the intended product. Yield: 7%

The gas chromatographic analysis of the reaction product before the acid treatment revealed that the constituents were nearly the starting materials alone except for the above-mentioned intended product.

$^1$HNMR (CDCl$_3$/TMS) δ: 2.15(s. 3H), 4.00(bs. 2H), 6.75(s. 1H), 7.19(s. 1H).

Example 22
Preparation of 4-heptafluoroisopropyl-N,2-dimethylaniline

A reaction was conducted in the same manner as in Example 1 for 2 hours except for using N,2-dimethylaniline in place of aniline to obtain the intended product. Yield: 88%

The gas chromatographic analysis of the reaction product before the acid treatment revealed that the constituents were nearly the starting materials alone except for the above-mentioned intended product.

$^1$HNMR (CDCl$_3$/TMS) δ: 2.16(s. 3H), 2.92(s. 3H), 6.63 (d. 1H), 7.23(s. 1H), 7.35(d. 1H).

Example 23
Preparation of 2-amino-5-heptafluoro-isopropylbiphenyl

A reaction was conducted in the same manner as in Example 1 for 9 hours except for using 2-aminobiphenyl in place of aniline to obtain the intended product. Yield: 85%

The gas chromatographic analysis of the reaction product before the acid treatment revealed that the constituents were nearly the starting materials alone except for the above-mentioned intended product.

$^1$HNMR (CDCl$_3$/TMS) δ: 3.80(bs. 2H), 6.83(d. 1H), 7.33(s. 1H), 7.36–7.52(m. 6H)

Example 24
Preparation of 4-heptafluoroisopropyl-2-phenoxyaniline

A reaction was conducted in the same manner as in Example 1 for 6 hours except for using 2-phenoxyaniline in place of aniline to obtain the intended product. Yield: 74%

The gas chromatographic analysis of the reaction product before the acid treatment revealed that the constituents were nearly the starting materials alone except for the above-mentioned intended product.

$^1$HNMR (CDCl$_3$/TMS) δ: 3.90(bs. 2H), 6.88(d 1H), 6.97(d 2H), 7.09(s, 1H), 7.11(t. 1H), 7.19(d. 1H), 7.34(dd. 2H).

Example 25
Preparation of 4-heptafluoroisopropyl-5-phenyl-2-anisidine

A reaction was conducted in the same manner as in Example 1 for 11 hours except for using 5-phenyl-2-anisidine in place of aniline to obtain the intended product. Yield: 52%

The gas chromatographic analysis of the reaction product before the acid treatment revealed that the constituents were nearly the starting materials alone except for the above-mentioned intended product.

$^1$HNMR (CDCl$_3$/TMS) δ: 3.89(s. 3H), 4.10(bs 2H), 6.51 (s. 1H), 6.89(s. 1H), 7.18(dd. 2H), 7.28–7.32(m. 3H)

Example 26
Preparation of 2-methyl-4-heptafluoro-isopropylaniline

In a flask for photo-reaction were placed 1.07 g (10 mmols) of 2-toluidine, 3.54 g (12 mmoles) of heptafluoroisopropyl iodide, 30 ml of 5% aqueous sodium hydrogen sulfite solution, 1.01 g (12 mmoles) of sodium hydrogen carbonate, 0.34 g (1 mmole) of tetrabutylammonium hydrogen sulfate and 20 ml of t-butyl methyl ether, and the resulting mixture was stirred under irradiation with a high pressure mercury lamp at room temperature for 2 hours. The reaction liquid was extracted with ethyl acetate and the organic layer was washed successively with dilute hydrochloric acid and water. The organic layer was dried with magnesium sulfate, then filtered and the organic solvent was distilled off under reduced pressure to obtain the intended product. Yield: 80%

The gas chromatographic analysis of the organic layer before the acid treatment showed that the starting materials had nearly disappeared, 2-methyl-4-heptafluoroisopropylaniline was 95% and 2-methyl-6-heptafluoroisopropylaniline was 1.6%, respectively in terms of area percentage, the ratio being 59:1.

Comparative Example 2
(Conducted at the Reaction Conditions Described in Reference B-b)

In a flask for photo-reaction were placed 3.54 g (33 mmoles) of 2-toluidine, 1 g (3.4 mmoles) of heptafluoroisopropyl iodide and 30 ml of 5% aqueous sodium hydrogen sulfide and the resulting mixture was stirred under irradiation with a high pressure mercury lamp at room temperature for 2 hours The reaction liquid was extracted with ethyl acetate and the organic layer was washed successively with dilute hydrochloric acid and water. The organic layer was dried with magnesium sulfate, the filtered and the organic solvent was distilled off under reduced pressure to obtain 0.37 g of a brown oily substance. Therein, the yield of 2-methyl-4-heptafluoroisopropylaniline was 15% in terms of area percentage by gas chromatographic analysis. In terms of area percentage, the ratio of 2-methyl-4-heptafluoroisopropylaniline to 2-methyl-6-heptafluoroisopropylaniline was 13:1; besides, 49% of unknowns were contained.

Example 27
Preparation of 2-methyl-4-heptafluoro-isopropylaniline

In a reaction vessel were placed 1.07 g (10 mmoles) of 2-toluidine, 3.54 g (12 mmoles) of heptafluoroisopropyl iodide, 3.03 g (12 mmoles) of sodium hydrogen carbonate, 0.34 g (1 mmole) of tetra-n-butylammonium hydrogen sulfate, 0.65 g (10 mmoles) of zinc dust and 20 ml of t-butyl methyl ether, then 20 ml of 5% aqueous sulfurous acid solution was added thereto with stirring, and the resulting mixture was stirred at room temperature for 2 hours.

The reaction liquid was extracted with ethyl acetate and the organic layer was washed successively with dilute hydrochloric acid and water. The organic layer was dried with magnesium sulfate, then filtered and the organic solvent was distilled off under reduced pressure to obtain the intended product. Yield: 81%

The gas chromatographic analysis of the organic layer before the acid treatment revealed that 4% of the starting materials remained and, in terms of area percentage, 2-methyl-4-heptafluoroisopropylaniline was 95% and 2-methyl-6-heptafluoroisopropylaniline was 1.6%, the ratio being 59:1.

Example 28
Preparation of 2-methyl-4-(2-nonafluoro-butyl)aniline

To a liquid mixture of 15 ml of water and 15 ml of t-butyl methyl ether were added successively 0.8 g (7.2 mmoles) of 2-toluidine, 2.0 g (5.8 mmoles) of 2-iodononafluorobutane, 1.0 g (6 mmoles) of sodium dithionite, 0.63 g (7.2 mmoles) of sodium hydrogen carbonate and 0.24 g (0.7 mmole) of tetra-n-butylammonium hydrogen sulfate, and the resulting mixture was allowed to react at room temperature for 5 hours. The organic layers were separated, then the aqueous layer was extracted with 20 ml of ethyl acetate, the organic layers were combined and washed successively with 2N aqueous hydrochloric acid, 5% aqueous sodium carbonate solution and saturated aqueous sodium chloride solution. The organic layer was dried with magnesium sulfate, then filtered and the organic solvent was distilled off under reduced pressure to obtain the intended product. Yield: 61%

$^1$HNMR (CDCl$_3$/TMS) δ: 2.20(s. 3H), 3.80(bs. 2H), 6.72(d. 1H), 7.23(s. 1H).

Example 29
Preparation of 4-t-butyl-2-heptafluoro-isopropylaniline

To a liquid mixture of 50 ml of water and 50 ml of ethyl acetate were added successively 3.0 g of t-butylaniline, 7.1 g of heptafluoroisopropyl iodide, 4.2 g of sodium dithionite, 2.0 g of sodium hydrogen carbonate and 0.8 g of tetrabutylammonium hydrogen sulfate, and the resulting mixture was stirred at room temperature for 15 hours. The organic layer was separated, then the aqueous layer was extracted with 50 ml of ethyl acetate, the organic layers were combined and washed successively with 2N aqueous hydrochloric acid, 5% aqueous sodium carbonate solution and saturated aqueous sodium chloride solution. The organic layer was dried with magnesium sulfate, then filtered, the organic solvent was distilled off under reduced pressure, and the residue was purified with a silica gel column to obtain the intended product. Yield: 77%

The gas chromatographic analysis of the reaction product before the acid treatment revealed that the constituents were nearly the starting materials alone except for the above-mentioned intended product.

$^1$HNMR (CDCl$_3$/TMS) δ: 1.26(s. 9H), 4.50(bs. 2H), 6.71(d. 1H), 7.28(s. 1H), 7.29(d. 1H).

Example 30
Preparation of 2-heptafluoroisopropyl-4-methylaniline

To a liquid mixture of 50 ml of water and 50 ml of ethyl acetate were added successively 3.3 g of p-toluidine, 10.7 g of heptafluoroisopropyl iodide, 6.3 g of sodium dithionite, 3.0 g of sodium hydrogen carbonate and 1.2 g of tetrabutylammonium hydrogen sulfate, and the resulting mixture was stirred at room temperature for 15 hours. The organic layer was separated, then the aqueous layer was extracted with 50 ml of ethyl acetate, the organic layers were combined and washed successively with 2N hydrochloric acid, 5% aqueous sodium carbonate solution and saturated aqueous sodium chloride solution. The organic layer was dried with magnesium sulfate, then filtered, the organic solvent was distilled off under reduced pressure, and the residue was purified with a silica gel column to obtain the intended product. Yield: 49%

The gas chromatographic analysis of the reaction product before the acid treatment revealed that the constituents were nearly the starting materials alone except for the above-mentioned intended product.

$^1$HNMR (CDCl$_3$/TMS) δ: 2.25(s. 3H), 4.20(bs. 2H), 6.67(d. 1H), 7.06(s. 1H), 7.07(d. 1H).

Example 31
Preparation of N,N-diethyl-4-heptafluoro-isopropylaniline

The same procedures as in Example 1 were followed except for using N,N-diethylaniline in place of aniline to obtain the intended product.

$^1$HNMR (CDCl$_3$/TMS) δ: 1.19(t. 6H), 3.38(dd. 4H), 6.69(d. 2H), 7.38(d. 2H).

Example 32

The same procedures as in Example 1 were followed to obtain the following anilines:

2-heptafluoroisopropyl-5-methoxyaniline,
$^1$HNMR (CDCl$_3$/TMS) δ: 3.78(s. 3H), 4.28(bs. 2H), 6.20(d. 1H), 6.35(m. 1H), 7.18(d. 1H).

3,5-dimethoxy-2-heptafluoroisopropylaniline,
$^1$HNMR (CDCl$_3$/TMS) δ: 3.73(s. 3H), 3.76(s. 3H), 3.93 (bs. 2H), 5.88(s 1H), 5.93(s. 1H).

3-fluoro-4-heptafluoroisopropyl-2-methylaniline,
$^1$HNMR (CDCl$_3$/TMS) δ: 2.08(d. 3H), 4.00(bs. 2H), 6.52(d. 1H), 7.20(t. 1H).

2,6-dichloro-4-heptafluoroisopropylaniline,
$^1$HNMR (CDCl$_3$/TMS) δ: 4.77(bs. 2H), 7.41(s. 2H).

2,6-dibromo-4-heptafluoroisopropylaniline,
$^1$HNMR (CDCl$_3$/TMS) δ: 4.88(bs. 2H), 7.51(s 2H).

4-heptafluoroisopropyl-3-methylthioaniline
$^1$HNMR (CDCl$_3$/TMS) δ: 2.41(s. 3H), 3.87(bs. 2H), 6.44(d. 1H), 6.53(s. 1H), 7.22(d 1H).

2-heptafluoro-5-methylthioaniline
$^1$HNMR (CDCl$_3$/TMS) δ: 2.44(s. 3H), 3.60(bs. 2H), 6.52(m. 1H), 6.61(m. 1H).

2-heptafluoroisopropyl-4-isopropylaniline
$^1$HNMR (CDCl$_3$/TMS) δ: 1.19(d. 6H), 2.74–2.87(m. 1H), 4.10(bs. 2H), 6.67(d. 1H), 7.10(s. 1H), 7.13(d. 1H).

2,5-dimethoxy-4-heptafluoroisopropylaniline
$^1$HNMR (CDCl$_3$/TMS) δ: 3.74(s. 3H), 3.82(s. 3H), 4.11 (bs. 2H), 6.35(s. 1H), 6.91(s. 1H).

2-heptafluoroisopropyl-5-methoxyaniline
Refractive index: nD 1.4488 (25.8° C.)
$^1$HNMR (CDCl$_3$/TMS) δ: 3.78(s. 3H), 4.28(bs. 2H), 6.20(d. 1H), 6.35(m. 1H, 7.18(d. 1H).

2,6-dimethyl-4-perfluoro-n-octylaniline,
m.p.: 100.2–102.2° C.

2-heptafluoroisopropyl-5-(1-hydroxyethyl)aniline,
Refraction index: nD 1.4320 (27.2° C.)

2-(N-benzyl-N-methylamino)-4-heptafluoroisopropyl-aniline,
Refraction index: nD 1.4940 (27.4° C.)

4-heptafluoroisopropyl-3-hydroxymethylaniline
$^1$HNMR (CDCl$_3$/TMS) δ: 3.96(bs. 2H), 4.815(t. 2H), 6.61(d. 1H), 7.05(s. 1H), 7.28(d. 1H).

4-heptafluoroisopropyl-2-(1-hydroxyethyl)aniline,
$^1$HNMR (CDCl$_3$/TMS) δ: 1.594(d. 3H), 4.61(bs. 2H), 4.94(dd. 1H), 6.70(d. 1H), 7.26(s 1H), 7.27(d 1H).

4-heptafluoroisopropyl-2-(4-methylpentan-2-yl)aniline,
$^1$HNMR (CDCl$_3$/TMS) δ: 0.884(d. 6H), 1.21(d. 3H), 1.35–1.47(m. 1H), 1.50–1.62(m. 2H), 1.72–1.84(m. 1H), 3.87(bs. 2H), 6.71(d. 1H), 7.20(d. 1H), 7.26(s. 1H).

3,5-dimethyl-2-heptafluoroisopropylaniline,
$^1$HNMR (CDCl$_3$/TMS) δ: 2.34(s. 3H), 2.44(d. 3H), 3.72 (bs. 2H), 6.41(bs. 2H).

4-heptafluoroisopropyl-N,N-di-2-hydroxyethylaniline,
$^1$HNMR (CDCl$_3$/TMS) δ: 3.62(t. 4H), 3.86(t. 4H), 6.72(d. 2H), 7.40(d. 2H).

N-ethyl-4-heptafluoroisopropyl-N-2-hydroxyethylaniline,
$^1$HNMR (CDCl$_3$/TMS) δ: 1.19(t. 3H), 1.89(bs. 1H), 3.46 (dd. 2H), 3.51(1.2H), 3.82(t.2H), 6.78(d. 2H), 7.39(d. 2H), 5-heptafluoroisopropylindoline,
$^1$HNMR (CDCl$_3$/TMS) δ: 3.08(t. 2H), 3.64(t. 2H), 4.10 (bs. 2H), 6.65(d. 1H), 7.23(d. 1H), 7.28(s. 1H).

N-acetyl-4-heptafluoroisopropyl-2-methylaniline,
m.p.: 132.7–136.2° C.
$^1$HNMR (CDCl$_3$/TMS) δ: 2.22(s. 3H), 2.33(s. 3H), 7.02 (bs. 1H), 7.41(s. 1H), 7.45(s. 1H), 7.61(d. 1H), 8.19(d. 1H).

4-heptafluoroisopropyl-N-methoxycarbonyl-2-methyl-aniline,
m.p.: 93.1–95.0° C.
$^1$HNMR (CDCl$_3$/TMS) δ: 2.30(s. 3H), 3.81(s. 3H), 6.52 (bs. 1H), 7.38(s. 1H), 7.45(d. 1H), 8.07(d. 1H).

N-tert-butoxycarbonyl-2-fluoromethyl-4-heptafluoro-isopropylaniline,
$^1$HNMR (CDCl$_3$/TMS) δ: 1.54(s. 9H), 5.47(d. 2H), 7.05 (bd. 1H), 7.45(s. 1H), 7.61(d. 1H), 8.19(4.1H)

N-tert-butoxycarbonyl-2-dimethylaminomethyl-4-heptafluoroisopropylaniline,
$^1$HNMR (CDCl$_3$/TMS) δ: 1.53(s. 9H), 2.23(s. 6H), 3.50 (s. 2H), 7.26(s. 1H), 7.47(d. 1H), 8.17(d. 1H), 9.90(s. 1H).

N-tert-butoxycarbonyl-4-heptafluoroisopropyl-2-hydroxymethylaniline,
$^1$HNMR (CDCl$_3$/TMS) δ: 1.53(s. 9H), 4.76(s. 2H), 7.36 (s. 2H), 7.52(d. 1H), 7.97(s. 1H), 8.18(d. 1H).

N-tert-butoxycarbonyl-2-chloromethyl-4-heptafluoro-isopropylaniline,
$^1$HNMR (CDCl$_3$/TMS) δ: 1.55(s. 9H), 4.64(s. 2H), 6.96 (s. 1H), 7.49(s. 1H), 7.58(d. 1H), 8.14(d. 1H).

4-heptafluoroisopropyl-2-methylthioaniline,
$^1$HNMR (CDCl$_3$/TMS) δ: 1.96(s. 3H), 3.69(s. 2H), 4.20 (bs. 2H), 6.76(d. 1H), 7.20(s. 1H), 7.31(d. 1H).

2-dimethylaminomethyl-4-heptafluoroisopropyl-N-methoxycarbonylaniline,
m.p.: 58.0–65.4° C.
$^1$HNMR (CDCl$_3$/TMS) δ: 2.25(s. 6H), 3.52(s. 2H), 3.78 (s. 3H), 7.26(s. 1H), 7.50(d. 1H), 8.20(d. 1H).

2-hydroxymethyl-4-heptofluoroisopropyl-N-methoxy-carbonylaniline,
$^1$HNMR (CDCl$_3$/TMS) δ: 2.38(bs. 1H), 3.79(s. 3H), 4.77(s. 2H), 7.36(d. 1H), 7.55(d. 1H), 8.18(d. 1H), 8.26(s. 1H).

4-heptafluoroisopropyl-N-hydroxycarbonylmethylaniline,
$^1$HNMR (CDCl$_3$/TMS) δ: 4.02(s. 2H), 6.66(d. 1H), 7.41 (d. 1H).

4-heptafluoroisopropyl-N-methoxycarbonylmethylaniline,
m.p.: 91.3–95.0° C.
$^1$HNMR (CDCl$_3$/TMS) δ: 3.81(s. 3H), 3.94(d. 2H), 4.59 (bs. 1H), 6.65(d. 2H), 7.40(d. 2H).

N-cyclopropylcarbonyl-2-heptafluoroisopropyl-4-methoxyaniline,
m.p.: 116–118° C.

N-acetyl-4-heptafluoroisopropyl-2-methylthioaniline,
$^1$HNMR (CDCl$_3$/TMS) δ: 2.26(s. 3H), 2.30(s. 3H), 7.50 (d. 1H), 7.70(s. 1H), 8.34(s. 1H), 8.49(d. 1H)

2-heptafluoroisopropyl-4-methoxyaniline,
$^1$HNMR (CDCl$_3$/TMS) δ: 3.72(s. 2H), 6.70(d. 1H), 6.81 (s. 1H), 6.87(dd. 1H).

4-heptafluoroisopropyl-2-hydroxy-5-methylaniline,
$^1$HNMR (CDCl$_3$/TMS) δ: 2.34(d. 3H), 3.87(bs. 2H), 6.57(s. 1H), 7.814(s. 1H).

4-heptafluoroisopropyl-5-hydroxymethyl-2-methylaniline
$^1$HNMR (CDCl$_3$/TMS) δ: 1.74(brs. 1H), 2.17(s. 3H), 3.88(brs. 2H), 4.78(d. 2H), 7.00(s. 1H), 7.14(s. 1H).

4-acetyl-2-heptafluoroisopropylaniline
$^1$HNMR (CDCl$_3$/TMS) δ: 2.50(s. 3H), 4.81(brs. 2H), 6.71(m. 1H), 7.85(d. 1H), 7.98(s. 1H).

2-ethyl-4-heptafluoroisopropyl-6-methylaniline
$^1$HNMR (CDCl$_3$/TMS) δ: 1.27(t. 3H), 2.215(s. 3H), 2.55 (dd. 2H), 3.85(brs. 2H), 7.15(brs. 2H).

Example 33

Preparation of 2-methyl-4-pentafluoro-ethylaniline

To a two-layer system liquid mixture of 10 ml of water and 10 ml of tetrahydrofuran were added successively 1.07 g (10 mmoles) of 2-toluidine, 2.46 g (10 mmoles) of perfluoroethyl iodide, 1.74 g (10 mmoles) of sodium dithionite, 0.84 g (10 mmoles) of sodium hydrogen carbonate and 0.34 (1 mmole) of tetrabutylammonium hydrogen sulfate, and the resulting mixture was stirred at room temperature for 2.5 hours. The organic layer was separated, then the aqueous layer was extracted with 20 ml of ethyl acetate, the organic layers were combined and washed successively with 2N aqueous hydrochloric acid, 5% aqueous sodium carbonate solution and saturated aqueous sodium chloride solution. The organic layer was dried with magnesium sulfate, then filtered, the organic solvent was distilled off under reduced pressure, and the residue was purified by column chromatography to obtain the intended product. Yield: 40%

$^1$HNMR (CDCl$_3$/TMS) δ: 2.20(s. 3H), 3.85(brs. 2H), 6.695(d. 1H), 7.24(d. 1H), 7.25(s. 1H).

The gas chromatographic analysis of the organic layer before the acid treatment showed that, in terms of area percentage, starting materials remaining unreacted was 40% and, as for the products, 2-methyl-4-pentafluoroethyl-aniline was 47% and 2-methyl-6-pentafluoroethylaniline was 11%, the ratio being about 4.3:1; thus the present reaction exhibited a high selectivity.

Example 34
Preparation of 2-methyl-4-nonafluoro-butylaniline

A reaction was conducted in the same manner as in Example 33 for 22 hours except for using perfluorobutyl iodide in place of perfluoroethyl iodide and tert-butyl methyl ether in place of tetrahydrofuran. The gas chromatographic analysis of the organic layer before the acid treatment showed that, in terms of area percentage, remaining starting materials were 20%; as for the product, 2-methyl-4-nonafluorobutylaniline was 60% and 2-methyl-6-nonafluorobutylaniline was 12%, the ratio being about 5:1.

Example 35
Preparation of 2-methyl-4-perfluorooctyl-aniline

A reaction was conducted in the same manner as in Example 33 for 96 hours except for using perfluorooctyl iodide in place of perfluorobutyl iodide. The gas chromatographic analysis of the organic layer before the acid treatment showed that, in terms of area percentage, remaining starting materials were 7%; as for the product, 2-methyl-4-perfluorooctylaniline was 66% and 2-methyl-6-perfluorooctylaniline was 16%, the ratio being about 4:1.

Example 36
Preparation of 2,6-dimethyl-4-pentafluoro-ethylaniline

A reaction was conducted in the same manner as in Example 33 for 8 hours except for using 2,6-dimethylaniline in place of 2-toluidine and ter-butyl methyl ether in place of tetrahydrofuran to obtain the intended product Yield: 87%

$^1$HNMR (CDCl$_3$/TMS) δ: 2.21(s. 6H), 3.80(bs. 2H), 7.15(s. 2H)

Example 37
Preparation of 2,6-diethyl-4-pentafluoro-ethylaniline

A reaction was conducted in the same manner as in Example 35 for 8 hours except for using 2,6-diethylaniline in place of 2,6-dimethylaniline of Example 36 to obtain the intended product. Yield 94%

$^1$HNMR (CDCl$_3$/TMS) δ: 1.28(t. 6H), 2.55(q. 4H) 3.90 (bs. 2H), 7.16(s 2H).

Example 38
Preparation of 2-methyl-6-pentafluoroethyl-aniline

To a two-layer system liquid mixture of 10 ml of water and 10 ml of tetrahydrofuran were added 1.07 g (10 mmoles) of 2-toluidine, 2.46 g (10 mmoles) of perfluoroethyl iodide, 1.04 g (10 mmoles) of sodium hydrogen sulfite, 0.65 g (10 mmoles) of zinc and 0.84 g (10 mmoles) of sodium hydrogen carbonate, and the resulting mixture was stirred at room temperature for 3 hours. The organic layer was dried with magnesium sulfate. The gas chromatographic analysis of the organic layer showed that, in terms of area percentage, remaining starting materials were 46%; as for the products, 2-methyl-4-pentafluoroethylaniline was 41% and 2-methyl-6-pentafluoroethylaniline was 8%, the ratio being about 5:1.

Example 39
Preparation of 4-t-butyl-2-pentafluoroethyl-aniline

To a liquid mixture of 40 ml of water and 40 ml of ethyl acetate were successively added 2.2 g of 4-tert-butylaniline, 5.0 g of perfluoroethyl iodide, 3.1 g of sodium dithionite, 1.5 g of sodium hydrogen carbonate and 0.6 g of tetrabutylammonium sulfate, and the resulting mixture was stirred at room temperature for 15 hours. The organic layer was separated, then the aqueous layer was extracted with 20 ml of ethyl acetate, and the organic layer were combined and washed successively with 2N aqueous hydrochloric acid, 5% aqueous sodium carbonate solution and saturated aqueous sodium chloride solution. The organic layer was dried with magnesium sulfate, then filtered, the organic solvent was distilled off under reduced pressure and the residue was purified by column chromatography to obtain 0.7 g of the intended product Yield: 18%

The gas chromatographic analysis of the organic layer before the acid treatment revealed that the constituents were nearly the starting materials alone except for the above-mentioned intended product.

$^1$HNMR (CDCl$_3$/TMS) δ: 1.28(s. 9H), 4.20(bs. 2H), 6.72(dd. 1H), 7.34(d. 1H).

Example 40
Preparation of 2,6-dimethyl-4-heptafluoro-n-propylaniline

The same procedures as in Example 33 were followed to obtain 2,6-dimethyl-4-heptafluoro-n-propylaniline.

$^1$HNMR (CDCl$_3$/TMS) δ: 2.12(s. 6H), 3.87(bs. 2H), 7.13(s. 2H).

$^{19}$FNMR (CDCl$_3$) δ: −126.9(2F), −110.6(2F), −80.54 (3F).

In the same manner as described above, the following compounds were obtained:

2,6-dimethyl-4-nonafluoro-n-butylaniline,
$^1$HNMR (CDCl$_3$/TMS) δ: 2.21(s. 6H), 3.88(bs. 2H), 7.14(s. 2H).
$^{19}$FNMR (CDCl$_3$) δ: −126.15(2F), −123.2(2F), −109.9 (2F), −81.5(3F)

2,6-dimethyl-4-perfluoro-n-hexylaniline,
$^1$HNMR (CDCl$_3$/TMS) δ: 2.21(s. 6H), 3.88(bs. 2H), 7.14(s. 2H).
$^{19}$FNMR (CDCl$_3$) δ: −126.7(2F), −123.3(2F), −122.2 (2F), −122.1(2F), −109.7(2F), −81.3(3F).

2,6-diethyl-4-heptafluoro-n-propylaniline,
$^1$HNMR (CDCl$_3$/TMS) δ: 1.29(t. 3H), 2.56(dd. 2H), 3.955(bs. 2H), 7.16(s. 2H),
$^{19}$FNMR (CDCl$_3$) δ: −126.9(2F), −110.6(2F), −80.54 (3F).

2,6-diethyl-4-nonafluoro-n-butylaniline,
$^1$HNMR (CDCl$_3$/TMS) δ: 1.285(t. 3H), 2.554(dd. 2H), 3.95(bs. 2H), 7.16(s. 2H).
$^{19}$FNMR (CDCl$_3$) δ: −126.15(2F), −123.2(2F), −109.9 (2F), −81.6(3F).

2,6-diethyl-4-perfluoro-n-hexylaniline,
$^1$HNMR (CDCl$_3$/TMS) δ: 1.284(t. 3H), 2.554(dd. 2H), 7.155(s. 2H).
$^{19}$FNMR (CDCl$_3$) δ: −126.7(2F), −123.4(2F), −122.3 (2F), −122.1(2F), −109.7(2F), −81.3(3F).

2-hydroxymethyl-4-perfluoro-n-hexylaniline
$^1$HNMR (CDCl$_3$/TMS) δ: 4.71(s. 2H), 6.735(d. 2H), 7.26(s. 1H), 7.32(d. 1H).
$^{19}$FNMR (CDCl$_3$) δ: -126.65(2F), -123.3(2F), -122.4 (2F), -122.0(2F), -109.8(2F), -81.3(3F).
4-heptafluoroisopropyl-3-methoxyaniline
Refractive index: nD 1.4488 (25.8° C.)

Example 41
Preparation of 4-heptafluoroisopropyl-N-(2-hydroxyethyl)-aniline
The intended product was obtained in the same manner as in Example 1 except for using 2-anilinoethanol as the starting material.
$^1$HNMR (CDCl$_3$/TMS) δ: 3.32(t. 2H), 3.85(t. 2H), 6.68(d. 2H), 6.37(d. 2H).

Example 42
Preparation of 4-heptafluoroisopropyl-2-hydroxy-5-methylaniline
The intended product was obtained in the same manner as in Example 1 except for using 2-hydroxy-5-methylaniline as the starting material.
$^1$HNMR (CDCl$_3$/TMS) δ: 2.34(d. 3H), 3.88(bs. 3H), 6.57(s. 1H), 6.814(s. 1H).

Reference Example 1
Preparation of 3-chloro-N$^1$-(2-chloro-4-heptafluoroisopropyl)-phenyl-N$^2$-isopropyl-phthalic acid diamide (hereinafter referred to as "reference compound 1")
In 10 ml of tetrahydrofuran was dissolved 0.45 g of 6-chloro-N-isopropyl-phthalic acid isoimide. To the solution was added 0.59 g of 2-chloro-4-heptafluoro-isopropylaniline and the resulting mixture was stirred for 1 hour to effect reaction. After completion of the reaction, the solvent of the reaction liquid was distilled off under reduced pressure, and the resulting residue was washed with ether-n-hexane to obtain 1.0 g of the intended product.
Physical property: m.p 204–206° C. Yield: 90%

Reference Example 2
Preparation of N$^1$-(2,6-dimethyl-4-pentafluoroethyl)phenyl-3-iodo-N$^2$-isopropyl-phthalic acid diamide (hereinafter referred to as "reference compound 2")
In 10 ml of tetrahydrofuran was dissolved 0.46 g of 6-iodo-N-isopropyl-phthalic acid isoimide. To the solution was added 0.29 g of 2,6-dimethyl-4-pentafluoroethylaniline and the resulting mixture was stirred for 1 hour to effect reaction. After completion of the reaction, the solvent of the reaction liquid was distilled off under reduced pressure, and the resulting residue was washed with ether-n-hexane to obtain 0.64 g of the intended product.
m.p. 246–250° C., Yield: 95%

Reference Example 3
Insecticidal Effect on Diamondback Moth (*Plutella xylostella*)
Adult diamondback moths were released and allowed to oviposit on a Chinese cabbage seedling. Two days after the release, the seedling having eggs deposited thereon was immersed for about 30 seconds in a liquid chemical prepared by diluting a preparation containing the reference compound as an active ingredient to adjust the concentration to 500 ppm. After air-drying, the seedling was allowed to stand in a room thermostated at 25° C. Six days after the immersion, the hatched insects were counted and the mortality was calculated according to the following equation. The test was carried out with three replications.

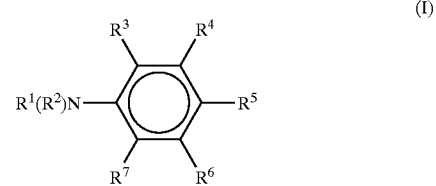

As a result, each of the reference compounds 1 and 2 in Reference Examples 1 and 2 was found to have a mortality of 100%, respectively.

Reference Example 4
Insaecticidal Effect on Common Cutworm (*Spodoptera litura*)
A piece of cabbage leaf (cultivar: Shikidori) was immersed for about 30 seconds in a liquid chemical prepared by diluting a preparation containing the reference compound as an active ingredient to adjust the concentration to 500 ppm. After air-drying, the piece was placed in a plastic Petri dish with a diameter of 9 cm whose bottom had been covered with a wetted filter paper. The piece was inoculated with third-instar larvae of common cutworm and the Petri dish was allowed to stand in a room thermostated at 25° C. and having a relative humidity of 70%. Four days after the inoculation, the dead and alive were counted and the mortality was calculated according to the equation described in Reference Example 2. The test was carried out with three replications of 10 insects.
As a result, each of the reference compounds 1 and 2 in Reference Examples 1 and 2 was found to have a mortality of 100%.

What is claimed is:
1. An aniline compound represented by the formula (I)

wherein R$^1$ denotes a hydrogen atom, R$^2$ denotes a hydrogen atom, (C$_{1-12}$)alkyl group, (C$_{3-8}$)cycloalkyl group, hydroxy (C$_{1-12}$)alkyl group, hydroxycarbonyl (C$_{1-12}$) alkyl group, (C$_{1-6}$)alkoxycarbonyl (C$_{1-6}$)alkyl group, —COR$^8$ (wherein R$^8$ is a hydrogen atom, (C$_{1-12}$)alkyl group, halo(C$_{1-12}$)alkyl group, (C$_{3-8}$)cycloalkyl group, phenyl group or phenyl group substituted with 1–5 groups, which are the same or different, selected from the group consisting of cyano group, nitro group, hydroxyl group, halogen atom, (C$_{1-6}$)alkyl group, halo(C$_{1-6}$)alkyl group, (C$_{1-6}$)alkoxy group, halo(C$_{1-6}$)alkoxy group, carboxyl group and (C$_{1-6}$) alkoxycarbonyl group) or COOR$^9$ (wherein R$^9$ is a (C$_{1-6}$)alkyl group, halo(C$_{1-6}$)alkyl group, phenyl group, phenyl group substituted with 1–5 groups, which are the same or different, selected from the group consisting of cyano group, nitro group, hydroxyl group, halogen atom, (C$_{1-6}$)alkyl group, halo(C$_{1-6}$)alkyl group, (C$_{1-6}$) alkoxy group, halo (C$_{1-6}$) alkoxy group, carboxyl group and (C$_{1-6}$)alkoxycarbonyl group, benzyl group or benzyl group substituted on the ring with 1–5 groups, which are the same or different, selected from the group consisting of cyano group, nitro group, hydroxyl group, halogen atom, $(C_{1-6})$alkyl group, halo$(C_{1-6})$alkyl group, $(C_{1-6})$alkoxy group, halo $(C_{1-6})$alkoxy group, carboxyl group and $(C_{1-6})$alkoxy-carbonyl group);

$R^3$, $R^4$, $R^6$ and $R^7$ are the same or different and each denote a hydrogen atom, halogen atom, hydroxyl group, $(C_{1-12})$alkyl group, halo$(C_{1-12})$alkyl group, halo $(C_{1-12})$alkoxy group, $(C_{1-12})$alkylthio group, halo$(C_{1-12})$alkylthio group, $(C_{1-6})$alkylthio $(C_{1-6})$alkyl group, hydroxy$(C_{1-6})$ alkyl group, amino $(C_{1-6})$ alkyl group, amino$(C_{1-6})$alkyl group substituted with one or two $(C_{1-6})$alkyl groups which are the same or different, phenyl group, phenyl group substituted with 1–5 groups, which are the same or different, selected from the group consisting of cyano group, nitro group, halogen atom, $(C_{1-6})$alkyl group, halo $(C_{1-6})$alkyl group, $(C_{1-6})$alkoxy group and halo $(C_{1-6})$alkoxy group, phenoxy group, phenoxy group substituted with 1–5 groups, which are the same or different, selected from the group consisting of cyano group, nitro group, halogen atom, $(C_{1-6})$alkyl group, halo$(C_{1-6})$alkyl group, $(C_{1-6})$alkoxy group, and halo $(C_{1-6})$alkoxy group, benzyl group, benzyl group substituted on the ring with 1–5 groups, which are the same or different, selected from the group consisting of cyano group, nitro group, halogen atom, $(C_{1-6})$alkyl group, halo$(C_{1-6})$alkyl group, $(C_{1-6})$alkoxy group and halo$(C_{1-6})$alkoxy group, —N$(R^{10})R^{11}$ (wherein $R^{10}$ and $R^{11}$ are the same or different and are each a hydrogen atom, $(C_{1-12})$alkyl group, $(C_{1-6})$cycloalkyl group, phenyl group, phenyl group substituted with 1–5 groups, which are the same or different, selected from the group consisting of cyano group, nitro group, hydroxyl group, halogen atom, $(C_{1-6})$alkyl group, halo $(C_{1-6})$alkyl group, $(C_{1-6})$ alkoxy group, halo$(C_{1-6})$alkoxy group, carboxyl group and $(C_{1-6})$alkoxycarbonyl group, benzyl group, benzyl group substituted on the ring with 1–5 groups, which are the same or different, selected from the group consisting of cyano group, nitro group, hydroxyl group, halogen atom, $(C_{1-6})$alkyl group, halo$(C_{1-6})$alkyl group, $(C_{1-6})$ alkoxy group, halo $(C_{1-6})$ alkoxy group, carboxyl group and $(C_{1-4})$alkoxycarbonyl group, —COR$^8$, wherein $R^8$ as the same meaning as defined above, or —COOR$^9$, wherein $R^9$ as the same meaning as defined above, further $R^{10}$ and $R^{11}$ conjointly form a $(C_{3-6})$alkylene group), or $(C_{2-27})$perfluoroalkyl group; and further, $R^1$ or $R^2$ and $R^3$ or $R^7$ conjointly form a $(C_{2-4})$alkylene group, and $R^3$, $R^4$, $R^5$, $R^6$ and $R^7$ form, with their two adjacent substituents joined together, a $(C_{3-5})$alkylene group or $(C_{1-2})$alkylenedioxy group, and $R^5$ denotes, a straight-chained $(C_{2-27})$perfluoroalkyl group; provided that (1) when $R^1$, $R^2$, $R^4$ and $R^7$ are each a hydrogen atom, $R^3$ is a fluorine atom and $R^6$ is a hydrogen atom, fluorine atom or chlorine atom, or when $R^1$, $R^2$, $R^4$ and $R^7$ are each a hydrogen atom, $R^7$ is a fluorine atom and $R^4$ is a hydrogen atom, fluorine atom or chlorine atom, then $R^5$ not be a pentafluoroethyl group or heptafluoro-n-propyl group, (2) when $R^1$ and $R^2$ are each a hydrogen atom, $R^3$ is a methyl group and $R^4$, $R^6$ and $R^7$ are simultaneously each a hydrogen atom, or when $R^1$ and $R^2$ are each a hydrogen atom, $R^7$ is a methyl group and $R^3$, $R^4$ and $R^6$ are simultaneously each a hydrogen atom, then $R^5$ must not be a pentafluoroethyl group, heptafluoropropyl group or nonafluoro-n-butyl group, (3) when $R^1$, $R^2$, $R^4$, $R^6$ and $R^7$ are simultaneously each a hydrogen atom and $R^3$ is a chlorine atom or when $R^1$, $R^2$, $R^3$, $R^4$ and $R^6$ are simultaneously each a hydrogen atom and $R^7$ is chlorine atom, then $R^5$ must not be a pentafluoroethyl group, heptafluoropropyl group or nonafluoro-n-butyl group, (4) when $R^1$, $R^2$, $R^4$, $R^6$ and $R^7$ are simultaneously each a hydrogen atom and $R^3$ is an ethyl group, n-butyl group, trifluoromethyl group or pentafluoroethyl group, or when $R^1$, $R^2$, $R^3$, $R^4$ and $R^6$ are simultaneously each a hydrogen atom and $R^7$ is an ethyl group, n-butyl group, trifluoromethyl group or pentafluoroethyl group, then $R^5$ must not be a pentafluoroethyl group, (5) when $R^1$, $R^2$, $R^3$, $R^4$, $R^6$ and $R^7$ are simultaneously each a hydrogen atom, then $R^5$ must not be a perfluoro-n-$(C_{2-8})$alkyl group, and (6) when $R^1$ is an acetyl group and $R^2$, $R^3$, $R^4$, $R^6$ and $R^7$ are each a hydrogen atom, then $R^5$ must not be a pentafluoroethyl groups.

2. The aniline compound according to claim 1, represented by the formula (I), wherein $R^1$ denotes a hydrogen atom, $R^2$ denotes a hydrogen atom, $(C_{1-12})$alkyl group, $(C_{1-6})$cycloalkyl group, hydroxy $(C_{1-12})$ alkyl group, hydroxycarbonyl $(C_{1-12})$ alkyl group, $(C_{1-6})$alkoxycarbonyl $(C_{1-6})$alkyl group, —COR(wherein $R^8$ is a hydrogen atom, $(C_{1-12})$alkyl group, halo$(C_{1-12})$alkyl group, $(C_{3-8})$cycloalkyl group or phenyl group) or COOR$^9$ (wherein $R^9$ is a $(C_{1-6})$ alkyl group, halo $(C_{1-6})$alkyl group, phenyl group or benzyl group); $R^3$, $R^4$, $R^6$ and $R^7$ are the same or different and each denote a hydrogen atom, halogen atom, hydroxyl group, $(C_{1-12})$alkyl group, halo$(C_{1-12})$alkyl group, halo$(C_{1-12})$ alkoxy group, $(C_{1-12})$alkylthio group, halo$(C_{1-12})$alkylthio group, $(C_{1-6})$alkylthio$(C_{1-6})$alkyl group, hydroxy$(C_{1-6})$alkyl group, amino$(C_{1-6})$alkyl group, amino $(C_{1-6})$ alkyl group substituted with one or two $(C_{1-6})$ alkyl groups which are the same or different, phenyl group, phenyl group substituted with 1–5 groups, which are the same or different, selected from the group consisting of cyano group, nitro group, halogen atom, $(C_{1-6})$alkyl group, halo$(C_{1-6})$alkyl group, $(C_{1-6})$alkoxy group and halo $(C_{1-6})$alkoxy group, phenoxy group, phenoxy group substituted with 1–5 groups, which are the same or different, selected from the group consisting of cyano group, nitro group, halogen atom, $(C_{1-6})$alkyl group, halo$(C_{1-6})$alkyl group, $(C_{1-6})$alkoxy group and halo $(C_{1-6})$alkoxy group, benzyl group, —N$(R_{10})R^{11}$ (wherein $R^{10}$ and $R^{11}$ are the same or different and are each a hydrogen atom, $(C_{1-12})$alkyl group, $(C_{3-8})$cycloalkyl group, phenyl group, phenyl group substituted with 1–5 groups, which are the same or different, selected from the group consisting of cyano group, nitro group, hydroxyl group, halogen atom, $(C_{1-6})$alkyl group, halo$(C^{1-6})$alkyl group, $(C_{1-6})$alkoxy group, halo $(C_{1-6})$ alkoxy group, carboxyl group and $(C_{1-6})$alkoxycarbonyl group, benzyl group, benzyl group substituted on the ring with 1–5 groups, which are the same or different, selected from the group consisting of cyano group, nitro group, hydroxyl group, halogen atom, $(C_{1-6})$alkyl group, halo$(C_{1-6})$alkyl group, $(C_{1-6})$alkoxy group, halo $(C_{1-6})$alkoxy group, carboxyl group and $(C_{1-6})$ alkoxy-carbonyl group, —COR$^8$ wherein $R^8$ has the same meaning as defined above, or COOR$^9$ wherein $R^9$ has the same meaning as defined above, further, $R^{10}$ and $R^{11}$ conjointly form a $(C_{3-6})$alkylene group), or $(C_{2-16})$ perfluoroalkyl group; and $R^5$ denotes a straight-chained $(C_{2-16})$ perfluoroalkyl group.

* * * * *